United States Patent
Sakamoto (10) Patent No.: US 10,381,207 B2
(45) Date of Patent: Aug. 13, 2019

(54) DATA PROCESSING SYSTEM FOR CHROMATOGRAPHIC MASS SPECTROMETRY

(71) Applicant: SHIMADZU CORPORATION, Kyoto-shi, Kyoto (JP)

(72) Inventor: Yuki Sakamoto, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 125 days.

(21) Appl. No.: 14/914,736

(22) PCT Filed: Sep. 4, 2013

(86) PCT No.: PCT/JP2013/073760
§ 371 (c)(1),
(2) Date: Feb. 26, 2016

(87) PCT Pub. No.: WO2015/033397
PCT Pub. Date: Mar. 12, 2015

(65) Prior Publication Data
US 2016/0202219 A1   Jul. 14, 2016

(51) Int. Cl.
*H01J 49/00*   (2006.01)
*G01N 30/86*   (2006.01)
*G01N 30/72*   (2006.01)

(52) U.S. Cl.
CPC ...... *H01J 49/0036* (2013.01); *G01N 30/8679* (2013.01); *G01N 30/72* (2013.01); *H01J 49/004* (2013.01)

(58) Field of Classification Search
CPC . G01N 30/8679; G01N 30/72; H01J 49/0036; H01J 49/004
See application file for complete search history.

(56) References Cited

U.S. PATENT DOCUMENTS 5,453,613 A * 9/1995 Gray ............... H01J 49/025
250/281
8,046,171 B2 * 10/2011 Ecker ............... G16B 30/00
702/19

(Continued)

FOREIGN PATENT DOCUMENTS

GB   2503538 A * 1/2014 ......... H01J 49/0027
GB   2510520 A * 8/2014 ......... G01N 33/6848

(Continued)

OTHER PUBLICATIONS

Written Opinion for PCT/JP2013/073760 dated Dec. 17, 2013. [PCT/ISA/237].

(Continued)

*Primary Examiner* — Michele Fan
(74) *Attorney, Agent, or Firm* — Sughrue Mion, PLLC (57) ABSTRACT

For peak A detected on a chromatogram created based on data obtained by a product ion scan measurement of one characteristic ion species originating from a target compound, a mass spectrum is extracted, and this mass spectrum is subjected to a database search to extract candidates of the compound as a primary search result. Subsequently, for peak B detected on a chromatogram created based on data obtained by a product ion scan measurement of another characteristic ion species originating from the same target compound, a mass spectrum is extracted, and this mass spectrum is subjected to a database search, with the search range limited to the candidates extracted in the search result based on peak A, to further reduce the number of candidates. The result which has been narrowed in this manner is displayed, whereby the amount of labor for the compound identification by analysis operators is reduced.

4 Claims, 6 Drawing Sheets

(56) References Cited

U.S. PATENT DOCUMENTS

| | | | | |
|---|---|---|---|---|
| 2005/0063864 A1* | 3/2005 | Sano | G01N 33/6848 | 422/68.1 |
| 2006/0243900 A1* | 11/2006 | Overney | G01N 33/6848 | 250/284 |
| 2006/0284068 A1* | 12/2006 | Amirav | H01J 49/0036 | 250/282 |
| 2006/0289735 A1* | 12/2006 | Ohtake | H01J 49/004 | 250/282 |
| 2008/0272292 A1* | 11/2008 | Geromanos | G01N 30/7233 | 250/288 |
| 2009/0294645 A1* | 12/2009 | Gorenstein | G06F 19/703 | 250/282 |
| 2011/0204221 A1* | 8/2011 | Satake | H01J 49/0031 | 250/282 |
| 2011/0226941 A1* | 9/2011 | Gorenstein | G01N 30/7233 | 250/282 |
| 2011/0288779 A1* | 11/2011 | Satulovsky | H01J 49/0031 | 702/19 |
| 2012/0248305 A1* | 10/2012 | Noda | H01J 49/0013 | 250/288 |
| 2012/0261568 A1* | 10/2012 | Coon | G06F 19/18 | 250/282 |
| 2014/0183353 A1* | 7/2014 | Shimada | H01J 49/0036 | 250/282 |

FOREIGN PATENT DOCUMENTS

| | | |
|---|---|---|
| JP | 2012-159336 A | 8/2012 |
| WO | 2013081852 A1 | 6/2013 |

OTHER PUBLICATIONS

International Search Report for PCT/JP2013/073760 dated Dec. 17, 2013.

Communication dated Jul. 28, 2016, issued by the European Patent Office in corresponding European Application No. 13893133.2.

* cited by examiner

Fig. 1

Fig. 3A
CHROMATOGRAM

Fig. 3B
DATABASE SEARCH RESULT

| PRIMARY SEARCH RESULT | | |
|---|---|---|
| SIMI-LARITY | COMPOUND NAME | CAS |
| 95 | a | 123 |
| 90 | b | 456 |
| 80 | c | 789 |
| 70 | d | 012 |
| 50 | e | 234 |

⇨

| SECONDARY SEARCH RESULT | | |
|---|---|---|
| SIMI-LARITY | COMPOUND NAME | CAS |
| 95 | a | 123 |

⇨

| FINAL RESULT OUTPUT | | |
|---|---|---|
| SIMI-LARITY | COMPOUND NAME | CAS |
| 95 | a | 123 |

Fig. 4A
CHROMATOGRAM

Fig. 4B
DATABASE SEARCH RESULT

| PRIMARY SEARCH RESULT ||| | SECONDARY SEARCH RESULT ||| | FINAL RESULT OUTPUT |||
|---|---|---|---|---|---|---|---|---|---|---|
| SIMI-LARITY | COMPOUND NAME | CAS | | SIMI-LARITY | COMPOUND NAME | CAS | | SIMI-LARITY | COMPOUND NAME | CAS |
| 95 | a | 123 | | | | | | 95 | a | 123 |
| 90 | b | 456 | | | NONE | | | 90 | b | 456 |
| 80 | c | 789 | | | | | | 80 | c | 789 |
| 70 | d | 012 | | | | | | 70 | d | 012 |
| 50 | e | 234 | | | | | | 50 | e | 234 |

Fig. 5A
CHROMATOGRAM

Fig. 5B
DATABASE SEARCH RESULT

PRIMARY SEARCH RESULT

| SIMI-LARITY | COMPOUND NAME | CAS |
|---|---|---|
| 95 | a | 123 |
| 90 | b | 456 |
| 80 | c | 789 |
| 70 | d | 012 |
| 50 | e | 234 |

SECONDARY SEARCH NOT PERFORMED

PEAK B NOT USED DUE TO THREDHOLD (e.g. PEAK HEIGHT)

FINAL RESULT OUTPUT

| SIMI-LARITY | COMPOUND NAME | CAS |
|---|---|---|
| 95 | a | 123 |
| 90 | b | 456 |
| 80 | c | 789 |
| 70 | d | 012 |
| 50 | e | 234 |

DATA PROCESSING SYSTEM FOR CHROMATOGRAPHIC MASS SPECTROMETRY

CROSS REFERENCE TO RELATED APPLICATIONS

This application is a National Stage of International Application No. PCT/JP2013/073760 filed Sep. 4, 2013, the contents of all of which is incorporated herein by reference in its entirety.

TECHNICAL FIELD

The present invention relates to a data processing system for chromatographic mass spectrometry utilized for processing data collected with a chromatograph mass spectrometer consisting of a gas chromatograph, liquid chromatograph or other types of chromatograph combined with a triple quadrupole mass spectrometer (which is also called the "tandem quadrupole mass spectrometer"). More specifically, it relates to a data processing system for the identification or structural estimation of a compound contained in a sample.

BACKGROUND ART

A method called an MS/MS analysis (tandem MS analysis) is widely used as one of the mass spectrometric techniques for identification, structural analyses or quantitative determination of compounds having large molecular weights. There are various configurations of mass spectrometers designed for performing MS/MS analyses, among which the triple quadrupole mass spectrometer is comparatively simple structured as well as easy to operate and handle.

In a generally used triple quadrupole mass spectrometer, sample-derived ions generated in an ion source are introduced into a front quadrupole mass filter (which is often commonly represented as "Q1"). In the front quadrupole mass filter, an ion having a specific mass-to-charge ratio is selected as a precursor ion. This precursor ion is introduced into a collision cell containing an ion guide with four or more poles (this ion guide is often commonly represented as "q2"). A collision-induced dissociation gas, such as argon, is supplied to this collision cell, and the precursor ion collides with this CID gas in the collision cell, whereby the ion is fragmented into various kinds of product ions. These product ions are introduced into a rear quadrupole mass filter (which is often commonly represented as "Q3"). In the rear quadrupole mass filter, a product ion having a specific mass-to-charge ratio is selected. The selected product ion reaches a detector and is thereby detected.

Such a triple quadrupole mass spectrometer can be used independently. However, this device is often used in combination with a chromatograph, such as a gas chromatograph (GC) or liquid chromatograph (LC). In particular, in recent years, the gas chromatograph triple quadrupole mass spectrometer (which is hereinafter called the "GC-MS/MS" according to common practice) and liquid chromatograph triple quadrupole mass spectrometer (which is hereinafter called the "LC-MS/MS" according to common practice) have become vital devices in the field of microanalysis which is aimed at analyzing a sample containing a large number of compounds or a sample mixed with various foreign substances, as in the case of testing residual pesticides in foodstuffs, testing environmental pollutants, checking the concentration of medicinal chemicals in blood, or screening drugs or poisonous substances.

In general, chromatograph triple quadrupole mass spectrometers have multiple measurement modes for the MS/MS analysis, such as the MRM (multiple reaction monitoring) measurement mode, precursor ion scan measurement mode, product ion scan measurement mode, and neutral loss scan measurement mode (for example, see Patent Literature 1).

In the MRM measurement mode, the mass-to-charge ratio of the ion which is allowed to pass through the mass filter is fixed in each of the front and rear quadrupole mass filters so as to measure the intensity (amount) of a specific product ion generated by the fragmentation of a specific precursor ion.

In the precursor ion scan measurement mode, while the mass-to-charge ratio of the ion (product ion) which is allowed to pass through the rear quadrupole mass filter is fixed, the mass-to-charge ratio of the ion (precursor ion) which is allowed to pass through the front quadrupole mass filter is continuously varied over a predetermined range of mass-to-charge ratios. By this mode, a mass spectrum of various precursor ions which generate a specific product ion by the fragmentation within the collision cell can be obtained.

In the product ion scan measurement mode, while the mass-to-charge ratio of the ion (precursor ion) which is allowed to pass through the front quadrupole mass filter is fixed, the mass-to-charge ratio of the ion (product ion) which is allowed to pass through the rear quadrupole mass filter is continuously varied over a predetermined range of mass-to-charge ratios. By this mode, a mass spectrum of various product ions generated by the fragmentation of a specific precursor ion within the collision cell can be obtained.

In the neutral loss scan measurement mode, both the mass-to-charge ratio of the ion which is allowed to pass through the front quadrupole mass filter and that of the ion which is allowed to pass through the rear quadrupole mass filter are continuously varied in an interlocked fashion so as to constantly maintain the difference in the mass-to-charge ratio between the two ions respectively allowed to pass through the front and rear quadrupole mass filters (i.e. the neutral loss). By this mode, it is possible to investigate the combination of the precursor ion and product ion which produces a specific neutral loss by the fragmentation within the collision cell.

Each of the previously described measurement modes is appropriately used according to the purpose of the analysis, kind of sample, kind of compound to be analyzed, and other factors. For example, the precursor ion scan measurement mode is useful in the case of specifically investigating various compounds having a specific partial structure, since this mode enables the exhaustive detection of precursor ions having a specific partial structure resulting from the fragmentation of the original compound. In particular, in the case of a triple quadrupole mass spectrometer equipped with an ion source employing the electron ionization method in which a fragmentation associated with the ionization (i.e. the so-called "in-source decay") is likely to occur, the product ion scan measurement mode can be conducted as follows: An ion having a specific partial structure resulting from the fragmentation in the ion source is selected as the precursor ion. This precursor ion is further fragmented within the collision cell, and a mass spectrum of the generated product ions is obtained. By investigating the pattern of this mass spectrum, it is possible to distinguish between structural isomers, positional isomers or similar compounds which are identical in molecular weight and only different in chemical structure.

As noted earlier, the precursor ion scan measurement and product ion scan measurement are each useful for the estimation of the chemical structure of a compound. Therefore, in the case of identifying an unknown compound with a complex chemical structure or estimating its structure by means of a GC-MS/MS or LC-MS/MS, a method is widely used in which a precursor ion scan measurement or product ion scan measurement of a plurality of characteristic ion species originating from the compound concerned is performed and the spectrum patterns of a plurality of mass spectra obtained as a result of the measurements are compared with the spectrum patterns of the mass spectra collected in a database to determine the degree of matching and thereby identify the compound.

Figure 6A:
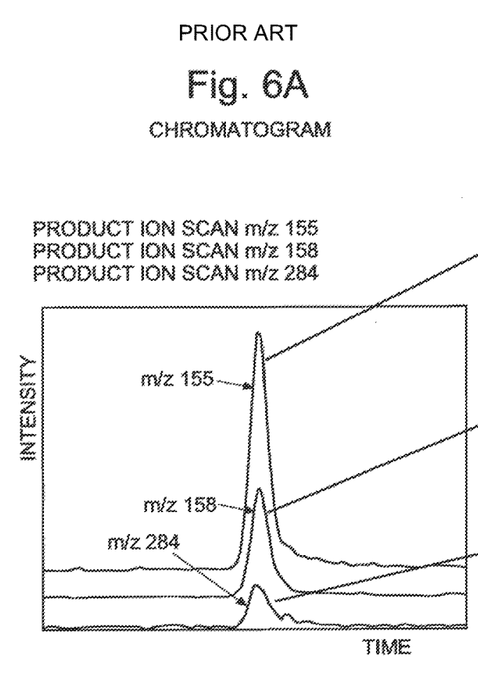
FIGS. 6A-6C illustrate the procedure of a conventional compound identification process.
Figure 6B:
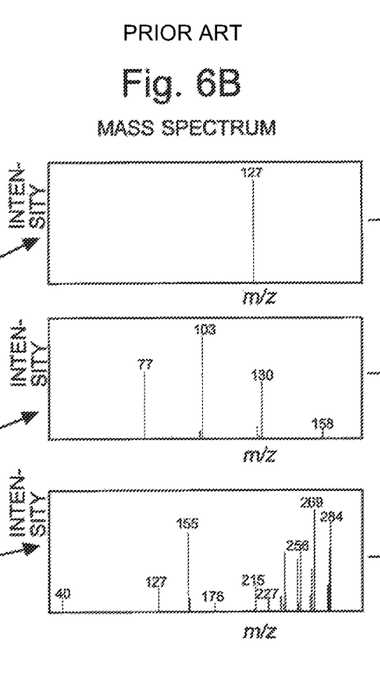
Figure 6C:
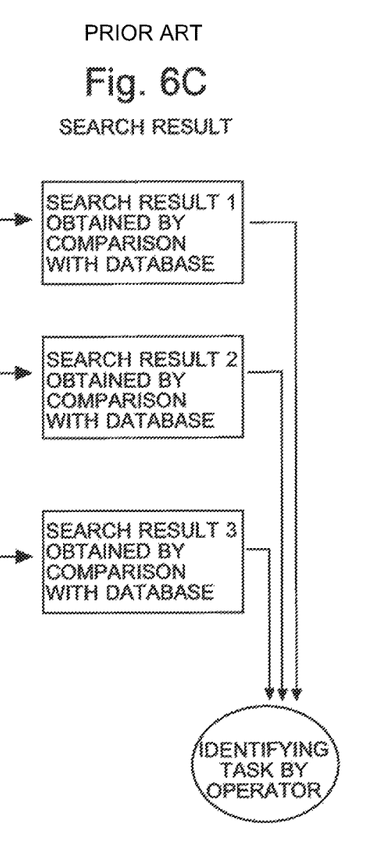

FIGS. 6A-6C show the procedure of such a conventional compound identification process. In the present example, three kinds of ions (m/z 155, m/z 158 and m/z 284) characteristic of the compound species which the compound to be identified belongs to are specified as the precursor ions, and the product ion scan measurement is performed. The signal intensities of the product ions obtained in each product ion scan measurement are added to create a chromatogram (total ion chromatogram), on which a peak appears at a retention time of the compound to be identified, as shown in FIG. 6A. In other words, if the retention times of the peaks detected on the respective chromatograms agree with each other, it is possible to estimate that those peaks are formed by the ions derived from the same compound. Accordingly, at the location where these peaks appear, or typically, at the peak-top position of these peaks, a mass spectrum (product ion spectrum) is extracted from each peak as shown in FIG. 6B, and each mass spectrum is individually compared with the database in which mass spectra of known compounds are collected. Consequently, as shown in FIG. 6C, three results of the database search are obtained. The analysis operator checks these search results and eventually identifies the compound, for example, by locating the compound candidates which have been found in all of these results.

CITATION LIST

Patent Literature

Patent Literature 1: JP 2012-159336 A

SUMMARY OF INVENTION

Technical Problem

In the previously described method, the analysis operator is considerably burdened with the task of personally checking and examining a plurality of database search results to identify the compound. In particular, in the case of medical chemicals, illegal drugs or similar compounds, there is a large number of compounds whose chemical structures have the same basic skeleton and differ from each other in the kind of substituent group or other minor portions, so that a considerable number of compound candidates will be found by the database search using a single mass spectrum. Therefore, even for an experienced analysis operator, the task of comparing a plurality of database search results to find a compound having the highest degree of matching is considerably cumbersome and easily leads to an incorrect judgment. Additionally, such a cumbersome task contributes to a decrease in the throughput of the screening or other processes.

The present invention has been developed to solve the previously described problem. Its objective is to provide a data processing system for chromatographic mass spectrometry which can reduce the burden on the analysis operator and improve the processing throughput in the task of identifying a compound or estimating its structure by a database search based on the results of the product ion scan measurement or precursor ion scan measurement of a plurality of ions originating from the same compound.

Solution to Problem

The present invention developed for solving the previously described problem is a data processing system for chromatographic mass spectrometry for processing chromatographic mass spectrometry data obtained by a precursor ion scan measurement and/or a product ion scan measurement of a plurality of different kinds of ions originating from one compound isolated by a chromatograph so as to identify the compound, the system including:

a) a primary extraction processor for extracting a candidate of the compound by comparing a mass spectrum obtained by the precursor ion scan measurement and/or the product ion scan measurement of one kind of ion originating from the target compound with a database;

b) a secondary extraction processor for performing, on the data obtained by the precursor ion scan measurement or the product ion scan measurement of each of the other ions specified for the target compound, the process of limiting the search range to the compound candidates extracted by the primary extraction processor and further reducing the number of compound candidates by comparing a mass spectrum obtained by the precursor ion scan measurement and/or the product ion scan measurement of another kind of ion originating from the target compound with the database; and c) a result output section for outputting a result of the process if there is a candidate remaining after the process of reducing the number of compound candidates by the secondary extraction processor is completed.

The chromatograph in the present invention is either a gas chromatograph or liquid chromatograph.

In the data processing system for chromatographic mass spectrometry data according to the present invention, the primary extraction processor creates a mass spectrum obtained by the precursor ion scan measurement and/or the product ion scan measurement of one kind of ion originating from a target compound to be identified. Then, for example, it compares the spectrum pattern of this mass spectrum with those of the mass spectra collected in a database and searches for compounds having similar mass spectra to extract compound candidates.

Subsequently, the secondary extraction processor limits the search range to the compound candidates extracted by the primary extraction processor and conducts a database search based on a mass spectrum obtained by the precursor ion scan measurement and/or the product ion scan measurement of another kind of ion originating from the target compound, so as to further reduce the number of compound candidates. If there are three or more kinds of ions which have been specified for the target compound, the database search with the narrowed search range is similarly performed to further reduce the number of compound candidates. After the process of reducing the number of compound candidates is performed one or more times by the secondary extraction processor, if there is one or more candidates remaining, the result output section outputs the result, for example, on the screen of a display monitor.

In this manner, the data processing system for chromatographic mass spectrometry according to the present invention can output an identification result which generally reflects the results of the database searches based on the mass spectra respectively obtained by the precursor ion scan measurement and/or product ion scan measurement of a plurality of kinds of ions specified for one compound.

As one mode of the data processing system for chromatographic mass spectrometry according to the present invention, the system may further preferably include a target mass spectrum selector for creating a chromatogram based on the data obtained by the precursor ion scan measurement and/or the product ion scan measurement for each of the various kinds of ions originating from the target compound, for detecting peaks having the same retention time on the created chromatograms, with each peak having a height or area equal to or higher than a predetermined threshold, and for subjecting only the mass spectra corresponding to the detected peaks to the database searches performed in the primary extraction processor and the secondary extraction processor.

As for the predetermined threshold used for judging the height or area of the peak, it is preferable to configure the system so that an analysis operator can appropriately set its value.

According to the present configuration, for example, if the amount of one of the plurality of precursor ions generated within the ion source as the target of the product ion scan measurement is too low to generate a sufficient amount of product ions from that precursor ion, the mass spectrum obtained from that precursor ion is not subjected to the database search in the primary extraction processor or the secondary extraction processor. Therefore, the final identification result is outputted using only the database search results obtained for the other ions.

Therefore, for example, even when some of the ion species originating from the target compound have not been detected with a sufficiently high level of sensitivity, the system can present possible candidates of the target compound to the analysis operator, instead of outputting a result which merely states that the compound is unidentifiable. The system can present possible candidates of any compound to the analysis operator if at least one of the plurality of previously specified ions can be detected with a sufficiently high level of sensitivity in the measurement of that compound. Therefore, for example, it is possible to perform a simultaneous multicomponent analysis by previously specifying one characteristic ion species for each of the various compounds.

In another preferable mode of the data processing system for chromatographic mass spectrometry according to the present invention, the primary extraction processor and the secondary extraction processor calculate the degree of similarity of a mass spectrum in the database search, and select the compound candidates under the condition that the degree of similarity should be equal to or higher than a predetermined threshold, while omitting the candidate-reducing process based on the mass spectrum if there is no candidate having the 10 degree of similarity equal to or higher than the predetermined threshold.

According to this configuration, if no compound which has a similar mass spectrum has been found by the database search based on the mass spectrum obtained by the precursor ion scan measurement and/or the product ion scan measurement of one or more kinds of ions, the search result is not adopted, and the final identification result is outputted using only the database search results obtained for the other ions.

Therefore, for example, even when no proper mass spectrum has been obtained for some of the ion species originating from the target compound, the system can present possible candidates of the target compound to the analysis operator, instead of outputting a result which merely states that the compound is unidentifiable.

Advantageous Effects of the Invention

By the data processing system for chromatographic mass spectrometry according to the present invention, when the identification or structural estimation is performed using the result of the product ion scan measurement or the precursor ion scan measurement of a plurality of ions originating from one compound, the database searches based on a plurality of mass spectra are automatically performed in a mutually related way. Therefore, the analysis operators themselves do not need to perform the cumbersome task of checking and comparing the database search results, so that the burden on the analysis operators for the identifying task is dramatically reduced. In addition, the present system can improve the throughput of the task of identifying a compound which has a complex chemical structure or for which there are a large number of other compounds having similar structures.

DESCRIPTION OF EMBODIMENTS

One embodiment of the GC-MS/MS system having a data processing system for chromatographic mass spectrometry according to the present invention is hereinafter described in detail with reference to the attached drawings.

Figure 1:
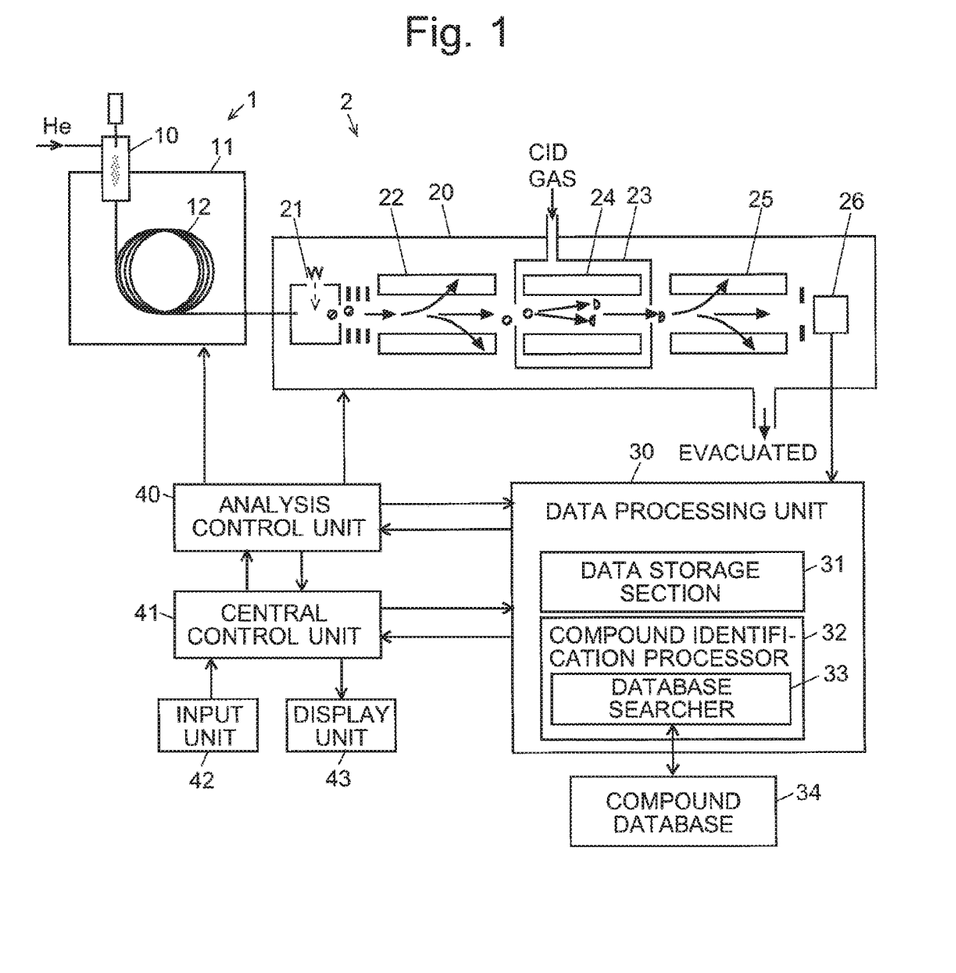
FIG. 1 is a schematic configuration diagram of one embodiment of the GC-MS/MS having a data processing system for chromatographic mass spectrometry according to the present invention.

As shown in FIG. 1, the GC-MS/MS system includes a GC unit 1 and an MS/MS unit 2. The GC unit 1 has a sample vaporization chamber 10 for vaporizing a trace amount of liquid sample, a column 12 for temporally separating sample components, and a column oven 11 for controlling the temperature of the column 12. The MS/MS unit 2 has the following devices placed within an analysis chamber 20 evacuated by a vacuum pump (not shown): an ion source 21 for ionizing a sample to be analyzed by electron ionization (EI); a front quadrupole mass filter 22 and a rear quadrupole mass filter 25, each of which is composed of four rod electrodes: a collision cell 23 with a multipole ion guide 24 placed inside: and a detector 26 for detecting an ion and producing a detection signal corresponding to the amount of the ion.

An analysis control unit 40 has the function of controlling the operations of each of the GC and MS/MS units 1 and 2 under the command of a central control unit 41. The central control unit 41, with an input unit 42 and a display unit 43 connected, is responsible for providing a user interface through these units and for conducting a general control of the entire system. A data processing unit 30 has, as its functional blocks, a data storage section 31 for storing the data collected by measurements and a compound identification processor 32, including a database searcher 33, for identifying a target compound using a compound database 34. In the compound database 34, mass spectra obtained by a product ion scan measurement with a plurality of characteristic ion species selected as the precursor ions (product ion spectra), and mass spectra obtained by a precursor ion scan measurement with a plurality of characteristic ion species selected as the product ions (precursor ion spectra) are previously recorded for each of the various compounds to be identified by the present system.

The central control unit 41 and the data processing unit 30 can be realized by using a personal computer as hardware and executing a dedicated controlling and processing software program installed on the same computer. In this case, a keyboard and a pointing device (e.g. mouse) correspond to the input unit 42, while a display monitor corresponds to the display unit 43.

A basic operation of the MS/MS analysis in the GC-MS/MS of the present embodiment is now roughly described.

When a trace amount of sample liquid is dropped into the sample vaporization chamber 10, the sample liquid quickly vaporizes. The compounds in the sample are carried into the column 12 by carrier gas (e.g. helium). While passing through the column 12, the compounds in the sample are delayed by different amounts of time and sequentially arrive at the exit port of the column 12. The column oven 11 is heated according to a previously determined temperature profile. The ion source 21 sequentially ionizes the compounds in the gas supplied from the exit port of the column 12. Since the ion source 21 is an EI ion source, some of the bonds in the compound are broken in the ionization process (i.e. a fragmentation of the compound occurs), whereby a plurality of kinds of ions are generated from various fragments derived from one compound.

In each of the front and rear quadrupole mass filters 22 and 25, a voltage that allows an ion having a specific mass-to-charge ratio to pass through the mass filter is applied to each rod electrode by the analysis control unit 40. Therefore, among the various ions derived from the compound, only an ion having the specific mass-to-charge ratio can pass through the front quadrupole mass filter 22 and be introduced into the collision cell 23. Meanwhile, a collision induced dissociation gas is introduced into the collision cell 23. The ion introduced into the collision cell 23 collides with this gas and becomes fragmented.

The various product ions generated by this fragmentation are introduced into the rear quadrupole mass filter 25 while being focused by the ion guide 24. Only a product ion having the specific mass-to-charge ratio can pass through the rear quadrupole mass filter 25 and reach the detector 26. The detection signal produced by the detector 26 is fed to the data processing unit 30. The data processing unit 30 creates a mass spectrum, mass chromatogram or other forms of information as well as performs the compound identification or other processes (as will be described later).

Similarly to commonly used GC-MS/MS systems, the present GC-MS/MS system has the following modes available for the MS/MS analysis: MRM measurement, product ion scan measurement, precursor ion scan measurement, and neutral loss scan measurement.

Next, the characteristic compound-identification process performed in the system of the present embodiment is described. In the hereinafter described example, in order to collect the data for the compound identification, a sample which contains a target compound is introduced into the GC unit 1. The sample gas containing various compounds separated in the GC unit 1 is introduced into the MS/MS unit 2, in which a product ion scan measurement with two kinds of ions characteristic of the target component specified as the precursor ions is repeatedly performed. The "ions characteristic of the target component" are the ions generated by the fragmentation due to the in-source decay when the target compound is ionized in the ion source 21. The signal intensity data which are obtained with the lapse of time by the product ion scan measurement over a predetermined range of mass-to-charge ratios are collectively stored in the data storage section 31.

Figure 2:
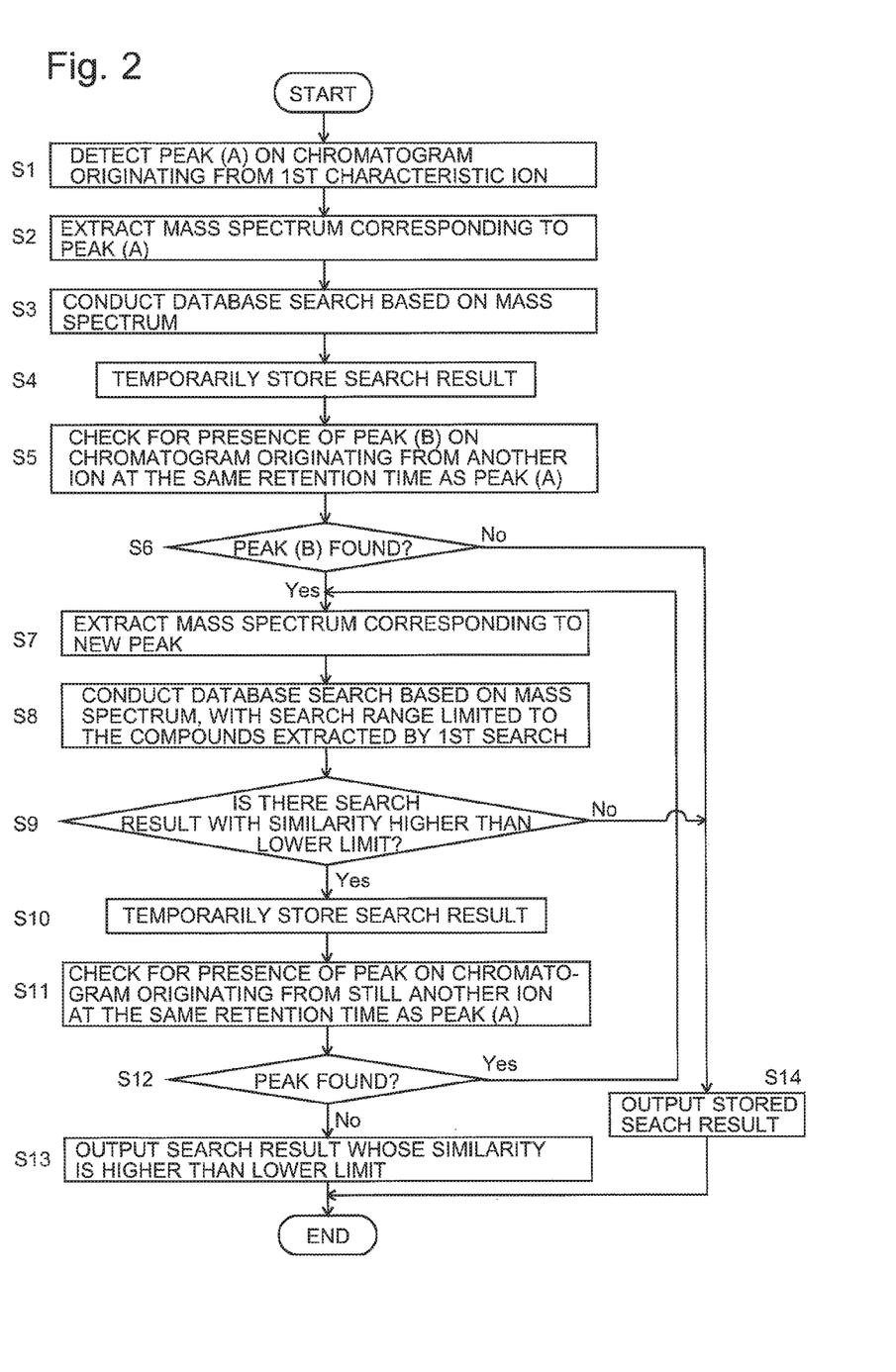
FIG. 2 is a flowchart of the compound identification process in the GC-MS/MS of the present embodiment.
Figure 3A:
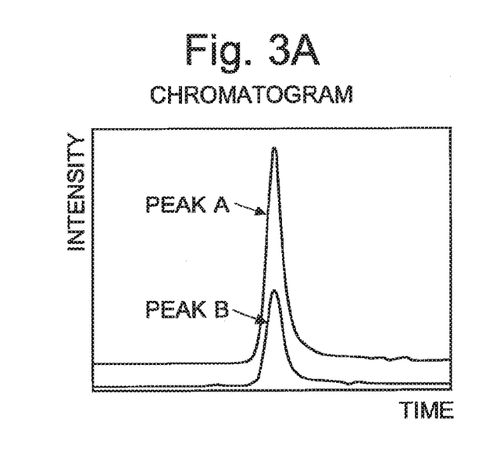
FIGS. 3A and 3B show one example of the compound identification process in the GC-MS/MS of the present embodiment.
Figure 3B:
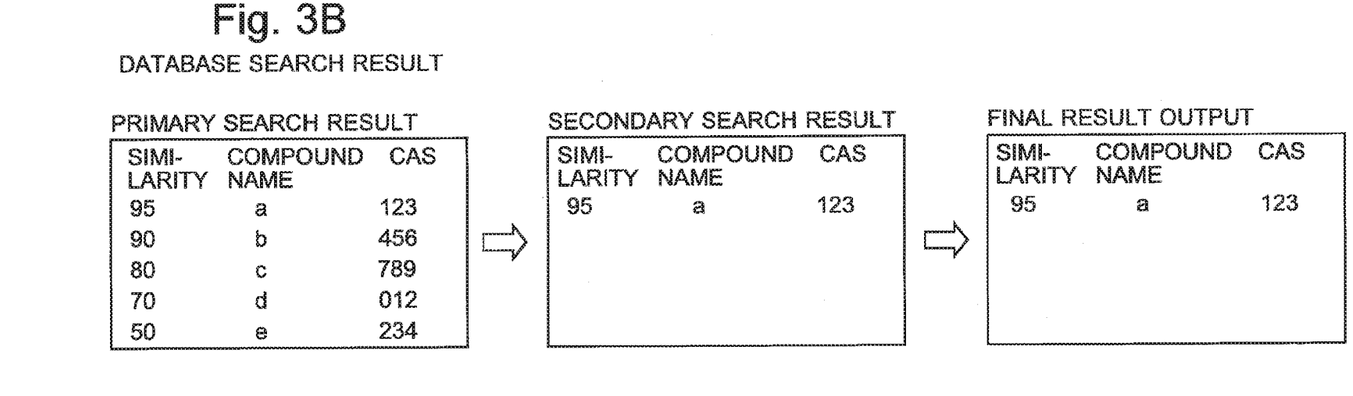
Figure 4A:
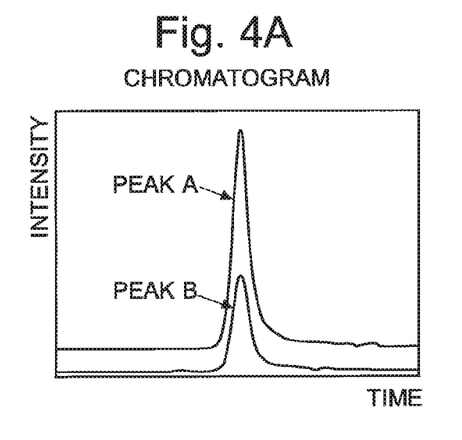
FIGS. 4A and 4B show another example of the compound identification process in the GC-MS/MS of the present embodiment.
Figure 4B:
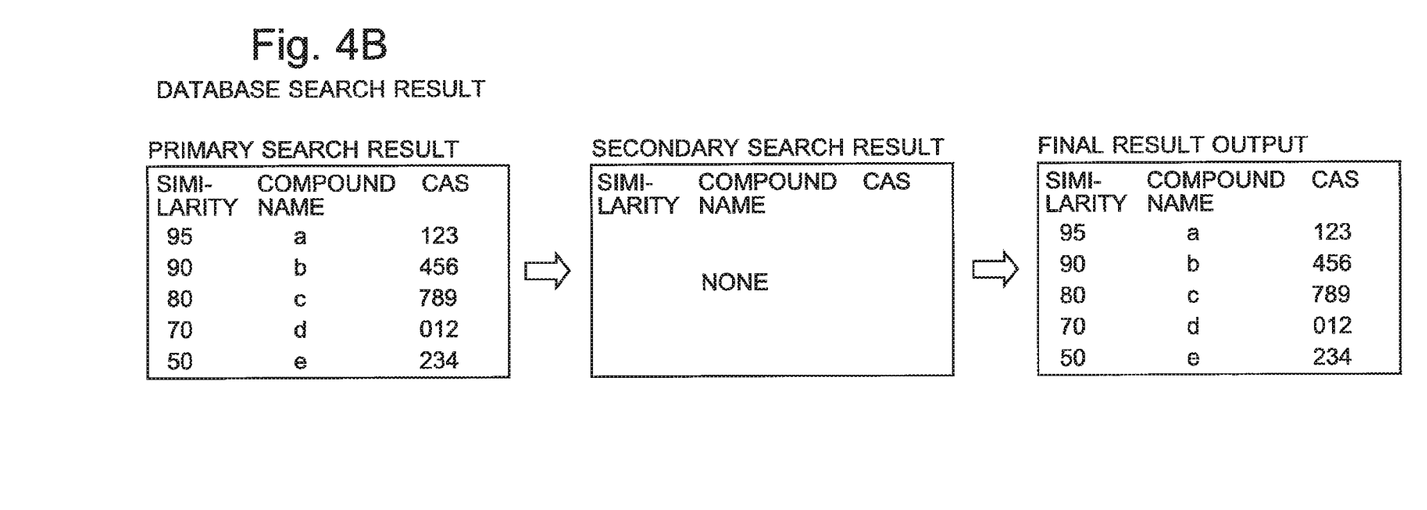
Figure 5A:
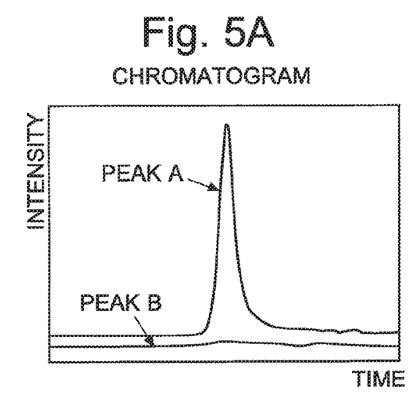
FIGS. 5A and 5B show another example of the compound identification process in the GC-MS/MS of the present embodiment.
Figure 5B:
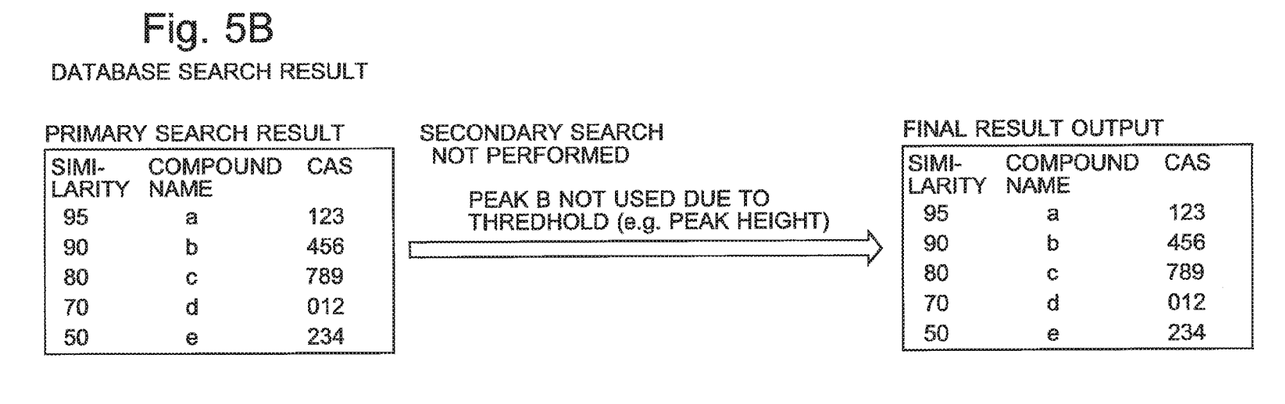

FIG. 2 is a flowchart showing the steps of the compound identification process performed in the compound identification processor 32. FIGS. 3A-5B show examples of the compound identification process, where FIGS. 3A, 4A and 5A show chromatogram waveforms, while FIGS. 3B, 4B and 5B show database search results.

When the identification process is initiated, the compound identification processor 32 sequentially reads, from the data storage section 31, time-series data obtained by the product ion scan measurement of a first characteristic ion originating from the target compound. For each point in time of the measurement, the same processor adds the signal intensities of the product ions over the predetermined mass-to-charge ratio range, and plots the added values in order of generation time to create a total ion chromatogram. Among the plurality of characteristic ions (in the present example, two ions), whichever ion may be designated as the first characteristic ion. For example, an ion having the largest mass-to-charge ratio among the specified precursor ions, or an ion from which a total ion chromatogram having a high peak (i.e. a high amount of ions) is obtained by the product scan ion measurement, may preferably be designated as the first characteristic ion.

On the chromatogram created in this manner, a peak is detected (Step S1). The peak detected in this step is hereinafter called "peak A". If no peak having a peak height or peak area equal to or greater than a predetermined threshold has been located on the chromatogram, the operation can proceed to Step S5, bypassing the processes of Steps S2 through S4 (which will be described later).

Subsequently, a mass spectrum (product ion spectrum) obtained at or near the peak top of peak A detected in Step S1 is extracted (Step S2). The database searcher 33 compares the spectrum pattern of this mass spectrum with those of the mass spectra (product ion spectra) collected in the compound database 34 to search for a compound having a highly similar spectrum pattern (Step S3). In this search, the degree of similarity of the spectrum pattern is calculated according to a predetermined algorithm, and any compound whose calculated degree of similarity is equal to or higher than a predetermined threshold is regarded as meeting the condition and extracted from the compound database 34. The extracted compounds are listed as the compound candidates, with the calculated degree of similarity related to the compound name or the CAS number. The list is temporarily stored in the internal memory (Step S4).

For example, consider the case where peak A has been detected on the chromatogram as shown in FIG. 3A, with five compounds "a", "b", "c", "d" and "e" listed as the candidates, as shown in the primary search result in FIG. 3B, as a result of the database search based on the mass spectrum corresponding to peak A. In the present example, the compounds with the degree of similarity of 50% or higher are listed as the candidates. No compound with the degree of similarity lower than 50% is registered in the list.

Subsequently, the compound identification processor 32 sequentially reads time-series data obtained by the product ion scan measurement of another characteristic ion originating from the target compound, and creates a total ion chromatogram in a similar manner to Step S1. Then, the same processor performs the peak detection on this chromatogram to determine whether or not there is a peak at the same retention time as the aforementioned peak A under the condition that the height or area of the peak should be equal to or higher than a predetermined threshold (Step S5). (The peak detected in this step is hereinafter called "peak B".) Any peak whose height or area is less than the threshold, as well as any peak whose retention time does not agree with that of peak A (or practically, whose retention time is displaced from that of peak A by an amount greater than a specific value) are considered as "no peak".

If it has been concluded that peak B is not present ("No" in Step S6), the operation proceeds to Step S14, where the database search result temporarily stored in the internal memory at that point, i.e. the list of the compound candidates, is outputted as the final search result on the screen of the display unit 43 via the central control unit 41. The example shown in FIGS. 5A and 5B is such a case: As shown in FIG. 5A, no peak B is present at the retention time of the peak A. In this case, the database search based on peak B, i.e. the secondary search, is not performed, and the primary search result stored in the internal memory is displayed as the final search result on the screen of the display unit 43. Since no reducing of the number of compound candidates is performed, the five compounds "a", "b", "c", "d" and "e" remain intact as the candidates on the list. However, at least the result of the database search based on peak A can be presented to the analysis operator.

In Step S6, if it has been concluded that peak B is present, the compound identification processor 32 extracts a mass spectrum (product ion spectrum) obtained at or near the peak top of the detected peak B (Step S7). The database searcher 33 compares the spectrum pattern of this mass spectrum with those of the mass spectra (product ion spectra) collected in the compound database 34 to search for a compound having a highly similar spectrum pattern (Step S8). In this step, unlike the database search in Step S3, not all of the compounds recorded in the compound database 34 are searched; the search range is limited to the compounds on the candidate list which has been extracted on the basis of peak A and stored in the internal memory, i.e. the five compounds "a", "b", "c", "d" and "e". Therefore, the number of compounds to be searched is far smaller than the number of all compounds recorded in the compound database 34, so that the database search can be completed in a considerably shorter period of time.

In the database search performed in Step S8, similarly to Step S3, the degree of similarity of the spectrum pattern is calculated according to the predetermined algorithm, and only the compounds whose degree of similarity is equal to or higher than a preset lower limit are selected. The compound identification processor 32 determines, as the secondary search result, whether or not there is any compound whose degree of similarity is equal to or higher than the lower limit (Step S9). If such a compound is present, the same processor once more lists the extracted compounds as the compound candidates, with the calculated degree of similarity related to the compound name or the CAS number, and temporarily stores the list in the internal memory (Step S10). In the example of FIGS. 3A and 3B, compound "a" is the sole compound whose calculated degree of similarity is equal to or higher than the lower limit of 50%. Accordingly, compounds "b", "c", "d" and "e" nominated in the primary search are removed from the selection, and the secondary search result which has been narrowed to the single compound "a" is held in the list.

On the other hand, FIGS. 4A and 4B show one example of the case where there is no compound whose degree of similarity calculated in the secondary search is equal to or higher than the lower limit of 50%. In this case, in Step S9, it is concluded that there is no compound which meets the condition, and the operation proceeds to Step S14. At this point, the list showing the primary search result is stored in the internal memory. Therefore, the primary search result is outputted as the final search result on the screen of the display unit 43 via the central control unit 41. That is to say, when no appropriate compound has been located by the database search based on peak B, the compounds located by the database search based on peak A can be presented to the analysis operator.

After the process of Step S10 has been completed, the compound identification processor 32 performs a similar process to Step S5; i.e. it reads the data obtained by the product ion scan measurement of still another characteristic ion originating from the target compound, creates a chromatogram based on the data, and performs the peak detection on the chromatogram (Step S11). If there is another peak at the same retention time as peaks A and B, the operation returns from Step S12 to Step S7 to once more perform the previously described processes from Step S7. If no such peak is present, or if in the first place there is no other characteristic ion originating from the target compound (as in the case of FIGS. 3A and 3B), the operation proceeds from Step S12 to Step S13, where the search result stored in the internal memory at that point, i.e. the list of one or more compounds whose degree of similarity is equal to or higher than the lower limit is displayed as the final search result on the screen of the display unit 43. In the example of FIG. 3B, the secondary search result is displayed on the screen of the display unit 43 as the final search result, i.e. the identification result.

As described thus far, in the GC-MS/MS system of the present embodiment, a plurality of database search results based on the mass spectra obtained using a plurality of kinds of ions originating from the target compound as the precursor ions are mutually related, and the thereby obtained result is eventually presented to the analysis operator. In the case where the number of compound candidates can be successfully reduced by the plurality of database searches, the narrowed result is presented to the analysis operator. Even when the number of compound candidates cannot be appropriately reduced by the plurality of database searches, a search result obtained using only significant database searches can be presented to the analysis operator.

The compound identification in the previously described example is performed by conducting the database search based on the mass spectra obtained by a plurality of product ion scan measurements. The compound identification can similarly be performed by conducting the database search based on the mass spectra obtained by a plurality of precursor ion scan measurements. It is also possible to perform the compound identification based on a combination of the database search based on a mass spectrum obtained by a precursor ion scan measurement and the database search based on a mass spectrum obtained by a product ion scan measurement.

In the previous embodiment, the lower limit for judging the degree of similarity of a mass spectrum as well as the threshold for judging the height or area of a peak in the process of detecting a peak on a chromatogram may be previously set, or the system may allow the analysis operator to manually set those values from the input unit 42.

In the previous embodiment, the data processing system for chromatographic mass spectrometry according to the present invention is applied in a GC-MS/MS. It is evident that the present invention is not only applicable to the data obtained with a GC-MS/MS but is also applicable to the data obtained with an LC-MS/MS.

It is also evident that any change, modification or addition appropriately made within the spirit of the present invention in any other aspects than those already described will fall within the scope of claims of the present application.

REFERENCE SIGNS LIST

1 . . . GC Unit
10 . . . Sample Vaporization Chamber
11 . . . Column Oven
12 . . . Column
2 . . . MS/MS Unit
20 . . . Analysis Chamber
21 . . . Ion Source
22 . . . Front Quadrupole Mass Filter
23 . . . Collision Cell
24 . . . Ion Guide
25 . . . Rear Quadrupole Mass Filter
26 . . . Detector
30 . . . Data Processing Unit
31 . . . Data Storage Section
32 . . . Compound Identification Processor
33 . . . Database Searcher
34 . . . Compound Database
40 . . . Analysis Control Unit
41 . . . Central Control Unit
42 . . . Input Unit
43 . . . Display Unit

The invention claimed is:

1. A chromatographic mass spectrometry system, comprising:
a chromatograph that isolates a target compound;
a mass spectrometer that obtains mass spectrometry data by performing a precursor ion scan measurement and/or a product ion scan measurement on a plurality of different ions originating from the target compound isolated by the chromatograph, and
a data processing system comprising:
a) a primary extraction processor for calculating a degree of similarity by comparing a mass spectrum obtained by the precursor ion scan measurement and/or the product ion scan measurement of one ion of the plurality of different ions with mass spectra in a database, and extracting one or more primary candidate of the target compound based on the degree of similarity being equal to or higher than a predetermined threshold;
b) a secondary extraction processor for performing, on the data obtained by the precursor ion scan measurement or the product ion scan measurement of each of other ions of the plurality of different ions, the process of limiting a search range to the one or more primary candidate extracted by the primary extraction processor, calculating a degree of similarity by comparing a mass spectrum obtained by the precursor ion scan measurement and/or the product ion scan measurement of another ion of the plurality of ions with the mass spectra in the database, and extracting one or more secondary candidate having the degree of similarity being equal to or higher than the predetermined threshold to reduce a number of the one or more candidates; and
c) a display for displaying a result of one or more secondary candidate if there is a secondary candidate remaining after the extraction by the secondary extraction processor is completed so as to identify the target compound.

2. The chromatographic mass spectrometry system according to claim 1, further comprising:
a target mass spectrum selector for creating a chromatogram based on the data obtained by the precursor ion scan measurement and/or the product ion scan measurement for each of various kinds of ions originating from the target compound, for detecting peaks having a same retention time on the created chromatograms, with each peak having a height or area equal to or higher than a predetermined threshold, and for subjecting only mass spectra obtained by the precursor ion scan measurement and/or the product ion scan measurement on the plurality of different ions corresponding to the detected peaks to the database searches performed in the primary extraction processor and the secondary extraction processor.

3. The chromatographic mass spectrometry system according to claim 2, wherein
a candidate-reducing process based on the mass spectrum is omitted if there is no candidate having the degree of similarity equal to or higher than the predetermined threshold.

4. The chromatographic mass spectrometry system according to claim 1, wherein a candidate-reducing process based on the mass spectrum is omitted if there is no candidate having the degree of similarity equal to or higher than the predetermined threshold.

\* \* \* \* \*